(12) United States Patent
Zhu et al.

(10) Patent No.: US 9,087,370 B2
(45) Date of Patent: Jul. 21, 2015

(54) FLOW DIVERTER DETECTION IN MEDICAL IMAGING

(71) Applicants: Reinhard Boese, Wuerzburg (DE); Ursula Boese, Wuerzburg (DE) Antje Schulte, Eckental (DE)

(72) Inventors: Ying Zhu, Monmouth Junction, NJ (US); Thomas Redel, Poxdorf (DE); Jan Boese

(73) Assignee: Siemens Aktiengesellschaft, Munich (DE)

( * ) Notice: Subject to any disclaimer, the term of this patent is extended or adjusted under 35 U.S.C. 154(b) by 42 days.

(21) Appl. No.: 13/899,850

(22) Filed: May 22, 2013

(65) Prior Publication Data

US 2014/0348408 A1 Nov. 27, 2014

(51) Int. Cl.
| | |
|---|---|
| G06K 9/00 | (2006.01) |
| G06T 7/00 | (2006.01) |
| A61B 6/03 | (2006.01) |
| A61B 6/00 | (2006.01) |
| A61B 8/06 | (2006.01) |

(52) U.S. Cl.
CPC ............... *G06T 7/0012* (2013.01); *A61B 6/032* (2013.01); *A61B 6/501* (2013.01); *A61B 6/507* (2013.01); *A61B 6/5211* (2013.01); *A61B 6/4441* (2013.01); *A61B 8/06* (2013.01)

(58) Field of Classification Search
CPC .... G06T 7/0012; A61B 6/032; A61B 6/4441; A61B 6/501; A61B 6/507; A61B 6/5211; A61B 8/06
See application file for complete search history.

(56) References Cited

U.S. PATENT DOCUMENTS

| | | | | |
|---|---|---|---|---|
| 6,285,739 | B1 * | 9/2001 | Rudin et al. | 378/98.8 |
| 8,073,229 | B2 * | 12/2011 | Huo et al. | 382/132 |
| 8,275,201 | B2 * | 9/2012 | Rangwala et al. | 382/173 |
| 8,311,308 | B2 * | 11/2012 | Chen et al. | 382/131 |
| 8,433,115 | B2 * | 4/2013 | Chen et al. | 382/128 |
| 8,463,007 | B2 * | 6/2013 | Steinberg et al. | 382/128 |
| 8,532,742 | B2 * | 9/2013 | Unal et al. | 600/424 |
| 8,542,902 | B2 * | 9/2013 | Ohishi | 382/131 |
| 8,622,911 | B2 * | 1/2014 | Hossack et al. | 600/439 |
| 8,737,725 | B2 * | 5/2014 | Wang et al. | 382/159 |
| 2010/0296709 | A1 * | 11/2010 | Ostrovsky-Berman et al. | 382/128 |
| 2011/0144480 | A1 * | 6/2011 | Lu et al. | 600/424 |
| 2011/0319927 | A1 * | 12/2011 | Nita | 606/200 |
| 2012/0002855 | A1 * | 1/2012 | Bai | 382/131 |
| 2013/0322725 | A1 * | 12/2013 | Enzmann et al. | 382/132 |
| 2014/0254900 | A1 * | 9/2014 | Sturm | 382/128 |
| 2014/0257087 | A1 * | 9/2014 | Elbasiony et al. | 600/424 |
| 2014/0270436 | A1 * | 9/2014 | Dascal et al. | 382/130 |

OTHER PUBLICATIONS

Zhu et al., "Deformable Motion Correction for Stent Visibility Enhancement", MICCAI 2011 Workshop: Computer Vision for Intravascular and Intracardiac Imaging Organizers, 2011.*

(Continued)

*Primary Examiner* — Katrina Fujita (57) ABSTRACT

A flow diverter is automatically detected from medical imaging data. The appearance of the flow diverter as represented in the data as well as the geometry or shape of the flow diverter is used in the detection. Using scoring for appearance relative to the centerline and cross-section of the centerline, the flow diverter is detected for increasing visualization.

18 Claims, 5 Drawing Sheets

(56) References Cited

OTHER PUBLICATIONS

M. Piotin et al., "Stent-Assisted Coiling of Intracranial Aneurysms: Clinical and Angiographic Results in 216 Consecutive Aneurysms," Stroke Journal of the American Heart Association, Webpage, http://stroke.ahajournals.org/content/41/1/110, pp. 1-7, 2010, printed Apr. 11, 2013.

J. Raymond et al., "Long-Term Angiographic Recurrences After Selective Endovascular Treatment of Aneurysms With Detachable Coils," Stroke Journal of the American Heart Association, Webpage, http://stroke.ahajournals.org/content/34/6/1398, pp. 1-7, 2003, printed Apr. 11, 2013.

B. Lubicz et al., "Flow-Diverter Stent for the Endovascular Treatment of Intracranial Aneurysms: A Prospective Study in 29 Patients with 34 Aneurysms," Stroke Journal of the American Heart Association, Webpage, http://stroke.ahajournals.org/content141/10/2247, pp. 1-8, 2010, printed Apr. 11, 2013.

T. F. Cootes et al., "Active Appearance Models," Proc. European Conference on Computer Vision 1998, vol. 2, pp. 484-498, 1998.

T. F. Cootes et al., "Active Shape Models—Their Training and Application," Computer Vision and Image Understanding, vol. 61, No. 1, pp. 38-59, 1995.

Y. Freund et al., "A Decision-Theoretic Generalization of On-Line Learning and an Application to Boosting*," Journal of Computer and System Sciences, vol. 55, pp. 119-139, 1997.

S.C. Yu et al., "Intracranial aneurysms: midterm outcome of pipeline embolization device—a prospective study in 143 patients with 178 aneurysms," Abstract, Radiology, pp. 1-2, 2012.

T. McInerney et al., Deformable Models in Medical Image Analysis: A Survey, Medical Image Analysis, 1(2), pp. 91-108, 1996.

P. Viola et al., "Rapid Object Detection using a Boosted Cascade of Simple Features," Accepted Conference on Computer Vision and Pattern Recognition 2001, pp. 511-518, 2001.

* cited by examiner

FLOW DIVERTER DETECTION IN MEDICAL IMAGING

BACKGROUND

The present embodiments relate to detecting a flow diverter in aneurysm treatment.

Aneurysms may be treated by placing an endovascular coil. Stent-assisted coil placement has been developed to address unfavorable aneurysm features, such as wide neck, large size, fusiform morphology, and post treatment recanalization. However, use of the coil may be associated with higher rates of aneurysm recurrence and procedure-induced mortality.

Figure 1:
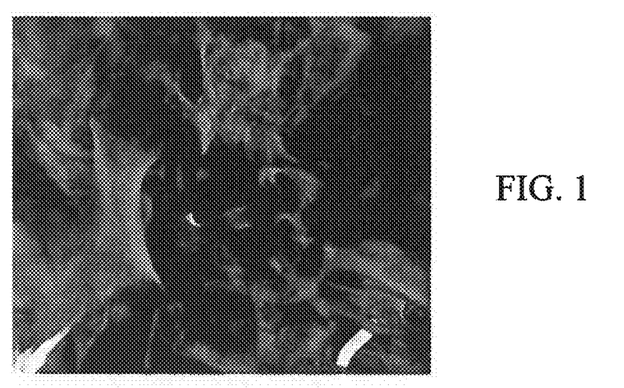
FIG. 1 is an example image of a brain region with a flow diverter.
Figure 2:
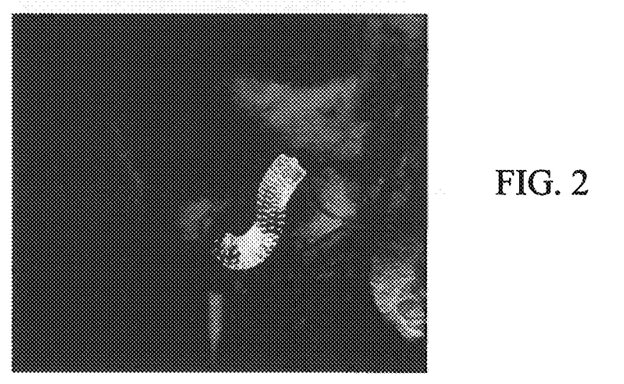
FIG. 2 is an example region of interest from the image of FIG. 1 where the visualization is adjusted to highlight the flow diverter.

Flow-diverting devices may overcome some of these problems. Endovascular placement of flow diversion devices as a treatment for intracranial aneurysms is gaining acceptance. In a flow diverter procedure, a stent or other flow diverter is placed to block the aneurysm. Following the procedure, a post-op x-ray (e.g., DynaCT by Siemens) scan is performed. The clinicians visually assess the outcome of the procedure. As FIG. 1 shows, a flow diverter, as a relatively small device, is embedded in surrounding tissues and is difficult to distinguish from tissue and other structure. The clinician may manually adjust the visualization to locate the flow diverter and make the flow diverter visible for clinical evaluation. FIG. 2 shows a close-up of the flow diverter in FIG. 1 after manual adjustment of the visualization. However, the manual adjustment is difficult and time consuming, resulting in increased costs.

BRIEF SUMMARY

By way of introduction, the preferred embodiments described below include methods, computer readable media and systems for flow diverter detection. The flow diverter is automatically detected from medical imaging data. The appearance of the flow diverter as represented in the data as well as the geometry or shape of the flow diverter is used in the detection. For example, using scoring for appearance relative to the centerline and cross-section of the centerline, the flow diverter is detected for increasing visualization.

In a first aspect, a method is provided for flow diverter detection in medical imaging. A processor identifies locations of centerline points of possible flow diverters from x-ray data representing a volume including the flow diverter. A centerline score is calculated for each of the possible flow diverters. The centerline score is a function of the location for the respective centerline point. The processor determines directions of centerlines passing through the centerline points for each of the possible flow diverters. A cross-section score is calculated for each of the possible flow diverters. The cross-section score is a function of the direction for the respective centerline. A first one of the possible flow diverters is selected as representing the flow diverter. The selecting is a function of the centerline scores and the cross-section scores. An image of the flow diverter is generated from the x-ray data. The flow diverter is highlighted relative to a background.

In a second aspect, a non-transitory computer readable storage medium has stored therein data representing instructions executable by a programmed processor for flow diverter detection. The storage medium includes instructions for obtaining data representing a brain region of a patient, detecting a flow diverter represented in the data as a function of appearance and three-dimensional shape of the flow diverter, and outputting an image of the flow diverter. The image of the flow diverter is a function of locations of the detected flow diverter.

In a third aspect, a system is provided for flow diverter detection. A C-arm x-ray scanner is configured to scan a patient with a flow diverter within the patient. A processor is configured to detect the flow diverter from data of the scan, the detection being a function of first and second likelihoods corresponding to first and second geometrical components of the flow diverter. The first geometrical component is different than the second geometrical component.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automatic flow diverter detection for modeling or visualization is provided. The workflow for visualizing a flow diverter is automated, assisting in the assessment of flow diverter placement in treating cerebral aneurysms. The detected flow diverter information may be used in a quantitative analysis and measurement of flow diverter placement.

Detection and segmentation of flow diverters is performed automatically by a hierarchical process of hypothesis generation, validation and fitting of a joint appearance and shape model. After a flow diverter is detected and isolated, an automatic windowing scheme may provide optimal visualization of the identified flow diverter.

Figure 3:
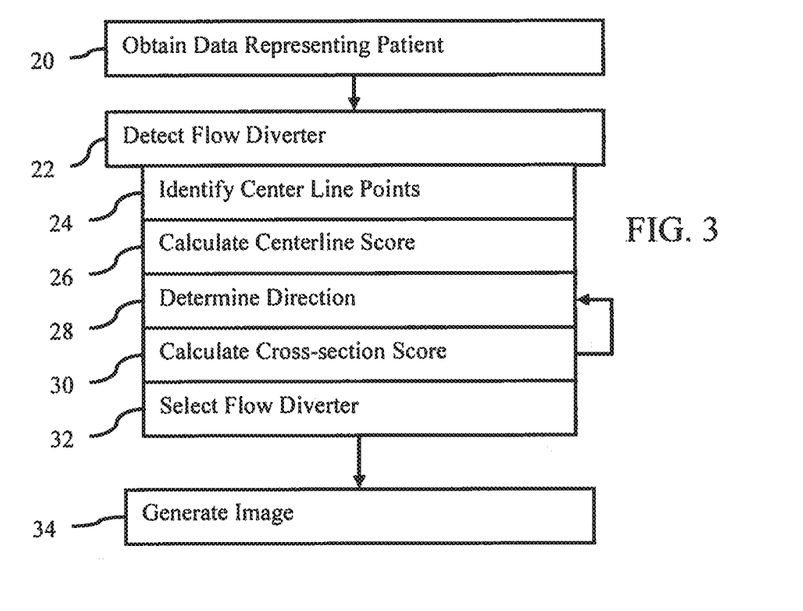
FIG. 3 is a flow chart diagram of one embodiment of a method for flow diverter detection.

FIG. 3 shows a method for flow diverter detection in medical imaging. The method is implemented by a medical diagnostic imaging system, a review station, a workstation, a computer, a PACS station, a server, combinations thereof, or other device for image processing medical diagnostic data.

Figure 9:
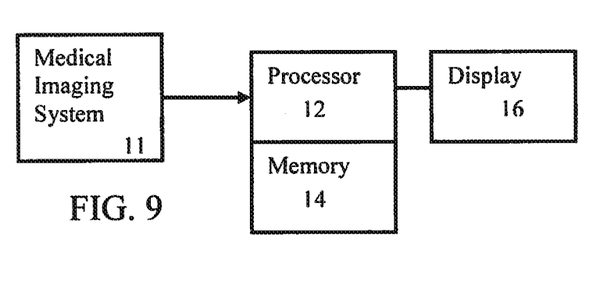
FIG. 9 is a block diagram of one embodiment of a system for flow diverter detection.

For example, the system, computer readable media, and/or processor shown in FIG. 9 implements the method, but other systems may be used.

Figure 4:
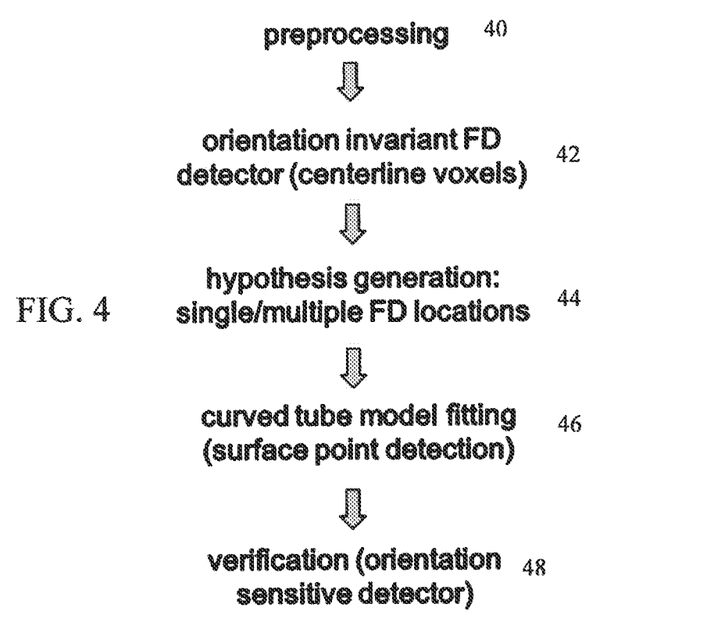
FIG. 4 illustrates another embodiment of a method for flow diverter detection.

FIG. 4 shows another embodiment of a method for flow diverter detection. FIGS. 3 and 4 represent overlapping of the same process or are alternative processes. The method of FIG. 4 is implemented by the same or different system described above for FIG. 3.

The methods are implemented in the order shown or a different order. For example, acts 26 and 30 are performed as part of or the output of performing acts 24 and 28, respectively. Additional, different, or fewer acts may be performed. For example, act 20 and/or act 34 are not performed. As another example, only one or both of acts 30 and 32 are performed. In another example, any of the acts of FIG. 4 may be performed in FIG. 3 or vice versa.

The acts are performed in real-time, such as during a surgical procedure to place the flow diverter. Performing during the procedure allows the clinician to determine proper placement relative to an aneurysm and/or proper functioning of the flow diverter. In other embodiments, the acts are performed after the procedure, such as performing as part of a review. The method may be repeated to provide comparative information over time.

The acts are performed automatically by a processor. The user causes the patient to be scanned or obtains scan data for the patient from a previous scan. The user may activate the process. Once activated, the method is performed without any user input indicating location of the flow diverter or other structure. User input of a region of interest without specifically identifying a location of the flow diverter may be used. Alternatively, the user assists in a semi-automated process, such as the user indicating possible locations of the flow diverter and/or further refining imaging after automated highlighting of the flow diverter. Other user input may be provided, such as for changing modeling parameter values, correcting detected locations, and/or to confirm accuracy.

In act 20, data representing a patient is obtained. The data is acquired by scanning the patient. Any type of medical imaging data may be used. For example, computed tomography (CT) like, C-arm x-ray, standard x-ray, or CT data is acquired for detecting the flow diverter. X-ray data is obtained. Any scanning sequence or approach may be used, such as using a C-arm to acquire CT like x-ray data in a DynaCT (Siemens). In other embodiments, magnetic resonance or other type of medical scan data is obtained.

In an alternative embodiment, the data is acquired by loading from memory. Data from a previously performed scan of the patient is stored in a memory, such as a picture archiving and communications system (PACS) database. The data is selected from the database. The data may be obtained by transfer, such as over a network or on a portable memory device.

The data represents a volume. The data is organized or formatted as a frame, set of data, sets of data, or other collection to represent the volume. The data represents locations distributed in three dimensions.

For flow diverter detection in aneurysm treatment, the data represents the all of or a portion of a patient's brain. Other structure may be represented as well, such as the skull, eyes, skin, and/or back bone. The data may be segmented to better identify a region, such as brain tissue.

In one embodiment, the data is a secondary reconstruction. A primary reconstruction is performed. Any type of reconstruction may be used. The primary reconstruction represents a relatively larger region of the patient, such as ½ or more of the brain. A region in which the flow diverter is likely to be is selected. The user or a processor identifies one or more features or relative spacing to select a region of interest. Another reconstruction based on the same or subsequently acquired data is performed, providing the secondary reconstruction. Any type of reconstruction for the more limited region may be used. The secondary reconstruction may provide data at a higher resolution in the more focused volume of interest around the aneurysm site than the primary reconstruction. In alternative embodiments, the primary reconstruction is used without the secondary reconstruction.

In act 40 of FIG. 4, the obtained data is preprocessed for performing the model-based method to automatically detect, segment and visualize the flow diverter. Any one or more preprocessing techniques may be used.

Since different scans and/or scanners may result in data at different resolutions and/or scales, the data is normalized. The data is smoothed and/or down sampled to provide a substantially common scale and resolution to the detector. Substantially accounts for tolerance and/or rounding. Reduced resolution may result in more efficient calculation through reduction in the amount of data to be processed. In other embodiments, the detection is performed on any scale and/or resolution or the scan and reconstruction are configured to output to the common scale and/or resolution.

Alternatively or additionally, the preprocessing defines a range of the data to be used. Since the flow diverter is metal, the signals from the flow diverter have more intensity than soft tissue. By only considering data with a higher intensity or intensity in a range around the material of interest, the data of interest for detection is isolated from some background information. Signal from bone, other tissues, or other objects may be included in the range. Due to scanning settings, different sets of data may have different intensities representing the same object. In one embodiment, a histogram is used. The peak intensity or group of intensities is identified. Any data representing intensities within a range from the peak (e.g., top 10% of the data) is maintained or used. The other data is not used or is removed.

In one embodiment, normalized resolution, secondary reconstruction data limited to higher intensities relative to the intensities in the obtained data is used for detection. Other combinations or no preprocessing are used in other embodiments.

In act 22 of FIG. 3, the obtained data is processed to detect the flow diverter represented therein. The detector is designed to detect the specific type of object, the flow diverter. The appearance and the shape of the flow diverter are used in detection.

The appearance is based on machine-learning and/or image processing. An appearance-based detector is learned from annotated flow diverter images to describe various local image patterns of flow diverters. Other measures indicating the appearance of the flow diverter in the data, such as pattern matching, may be used.

Figure 5:
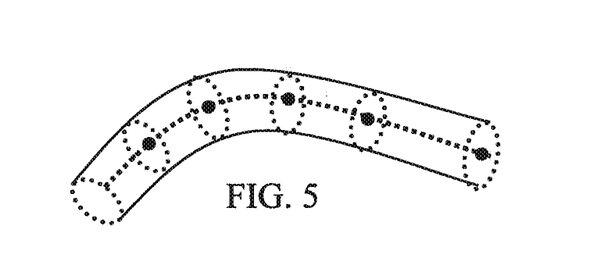
FIG. 5 is a graphical representation of an example shape model.

The shape is based on a three-dimensional shape model. The shape model describes the curved 3D tubular shape of a flow diverter. For example, the shape has a circular circumference and a gradually curving centerline. Other shape characteristics may be used. FIG. 5 shows one example of the shape model of a flow diverter. The centerline is represented by centerline points sampled along the centerline. The cross-section is represented by surface points at a radius from the centerline points. The shape of a placed flow diverter is modeled as a curved tube. In centerline tracing, a series of centerline points and associated radii are used as a representation of the shape. Assuming that there are M points on the centerline: $cl^{\Phi}\{x_i | i=1, \ldots, M\}$. Radius information is described by the parameter $\phi$. The point located at $x_i$ is denoted as $cl_i^\phi$. The centerline is described as a three-dimensional curve interpolated from or fit to these points. The outlines of the local cross sections centered at these centerline points form a set of surface points. A surface point $cs_i$ for a radius centered at point $x_i^c$ is described as $cs_i=(x_i,r,\theta)$, where r, is the radius of the cross section and is the normal vector. For simplicity, the model for the flow diverter, FD, is expressed as FD={$cl_i^\phi$, $cs_i$|i=1, . . . , M}. Other models may be used, where additional, different, or fewer geometrical characteristics are used.

To detect based on appearance and the geometrical model, scores for the different aspects and/or process acts based on the aspect are used. For example, scores for appearance centered around different possible centerline points in the data are calculated. Using the directional nature of the centerline and the round or generally circular cross-section or other geometrical consideration, scores for cross-sections orthogonal to the centerline at the centerline points (i.e., surface points) are calculated. Tracing along the centerline and corresponding cross-section definition for scoring provides multiple appearance and geometrical related scores.

Scoring is provided for multiple possible flow diverters. Multiple hypotheses are identified and ranked. The scoring provides the ranking for selecting the possible flow diverter or hypothesis as the actual flow diverter.

FIG. 3 shows the detection in acts related to identifying and scoring the centerline and tracing and scoring based on cross-sections for selecting the flow diverter. FIG. 4 shows the detection in acts for appearance based detection of centerline and curved tube fitting to different hypotheses flowed by selection in the form of verification. Both approaches represent the same or similar process.

In act 24 of FIG. 3, center line points are identified. The points are identified from the data representing the volume. Different locations throughout the volume are tested for corresponding to a center line point. The data in a region around the point is examined. Data in a window centered at the location is tested for appearing as a flow diverter. One or more locations spaced apart from each other may be identified as possible flow diverters, so multiple centerline points are identified. Similarly, one or more locations near each other (e.g., possibly part of the same flow diverter) may be identified as centerline points.

To identify the centerline points, an appearance-based flow diverter detector is applied in act 42 of FIG. 4. Any appearance-based detector may be used, such as matched filtering or template correlation. In one embodiment, a machine-learned detector or classifier is applied. The machine-learnt classifier is trained before application, such as days, weeks, months, or years before.

A set of training data from different patients is acquired. The training data is the same type and for the same or similar region as the obtained data. The training data is filtered or processed to obtain input features for the training and/or the training data itself is used as the input feature. Example input features for training include Haar, gradient, and/or steerable features. A large pool of features may be extracted. The large pool is determined by a programmer or may include features systematically determined. The training determines the most determinative features for a given classification and discards lesser or non-determinative features.

To prepare the set of training samples, actual flow detectors in a number of data sets are manually annotated or indicated for use as a ground truth. Any number of expert annotated sets of data is used.

The detector is trained from the training data set using a computer. A data-driven, learning-based algorithm is applied to the training data. Using machine learning, the classifier is trained. The machine-trained classifier is any one or more classifiers. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

Only one classifier is applied to detect the flow diverter. Alternatively, a series of classifiers are applied. A hierarchal or cascaded approach may be used, such as learning to detect different aspects of the appearance of the flow diverter individually. The detector may be trained to detect groups or joint model parameters from the detected individual possibilities. The joint context associated with possible groups of landmarks, surface, nodes, meshes or other parameters may be used. The individual classifier, joint classifier, or both classifiers use a machine-learnt model or models.

In one embodiment, the machine-trained classifier is a probabilistic boosting tree classifier. The detector is a tree-based structure with which the posterior probabilities of the presence of the centerline and/or surface (e.g., nodes of a mesh) are calculated from given data. Each detector not only provides a binary decision for a given sample, but also a confidence value (e.g., score) associated with the decision. The nodes in the tree are constructed by a nonlinear combination of simple classifiers using boosting techniques. The probabilistic boosting tree (PBT) unifies classification, recognition, and clustering into one treatment. Alternatively, a programmed, knowledge based, or other classifier without machine learning is used.

Once trained, a matrix is output. The matrix represents the learnt algorithm for detection from obtained data or features derived from the obtained data. For application, the obtained data or derived features from a specific patient are input to the matrix. As an output, the matrix indicates the location as having the appearance of the flow diverter or not. The output may also include probabilistic information, such as associated with a confidence or likelihood that the location is at a centerline of a flow diverter. The machine-learnt detector estimates the parameters of the model from the obtained data.

In one embodiment, the machine-learned detector is an orientation invariant segment detector. An orientation invariant FD segment detector is learned from examples of flow diverter image patches. To learn the flow diverter segment detector, positive training samples are taken from local flow diverter segments and rotated to a uniformly sampled set of orientations in the volume sphere to synthesize training examples of different orientation. Negative training samples are taken from surrounding tissues with high intensity values. A binary classification algorithm such as Adaboost, Randomized tree, or randomized forest is used to learn a binary classifier.

The binary classifier outputs a probability of the centerline point $p(cl_i^\phi)$ given the local (e.g., windowed) image content. For example, three-dimensional Haar features and context gradient features within a windowed region centered on the location are calculated from the obtained data. The context gradient feature is a measure of the gradients of neighboring points. Since the centerline is associated with fluid or response similar to tissue, it is the gradient of surrounding locations that may include the surface of the flow detector that indicate flow detector appearance. The context gradient measures the gradients of surrounding locations rather than the centered location. The Haar and context gradient features may capture the local appearance of the centerline. Other features may be used in addition or as alternatives.

A response map with scores for voxels of the x-ray data is generated. The window for testing for the flow diverter is moved to different locations within the volume. The response to the appearance test is determined for each window position. For example, the learned binary classifier is used as the orientation invariant flow diverter segment detector. The output of the detector is a response map indicating results for each location.

Figure 6:
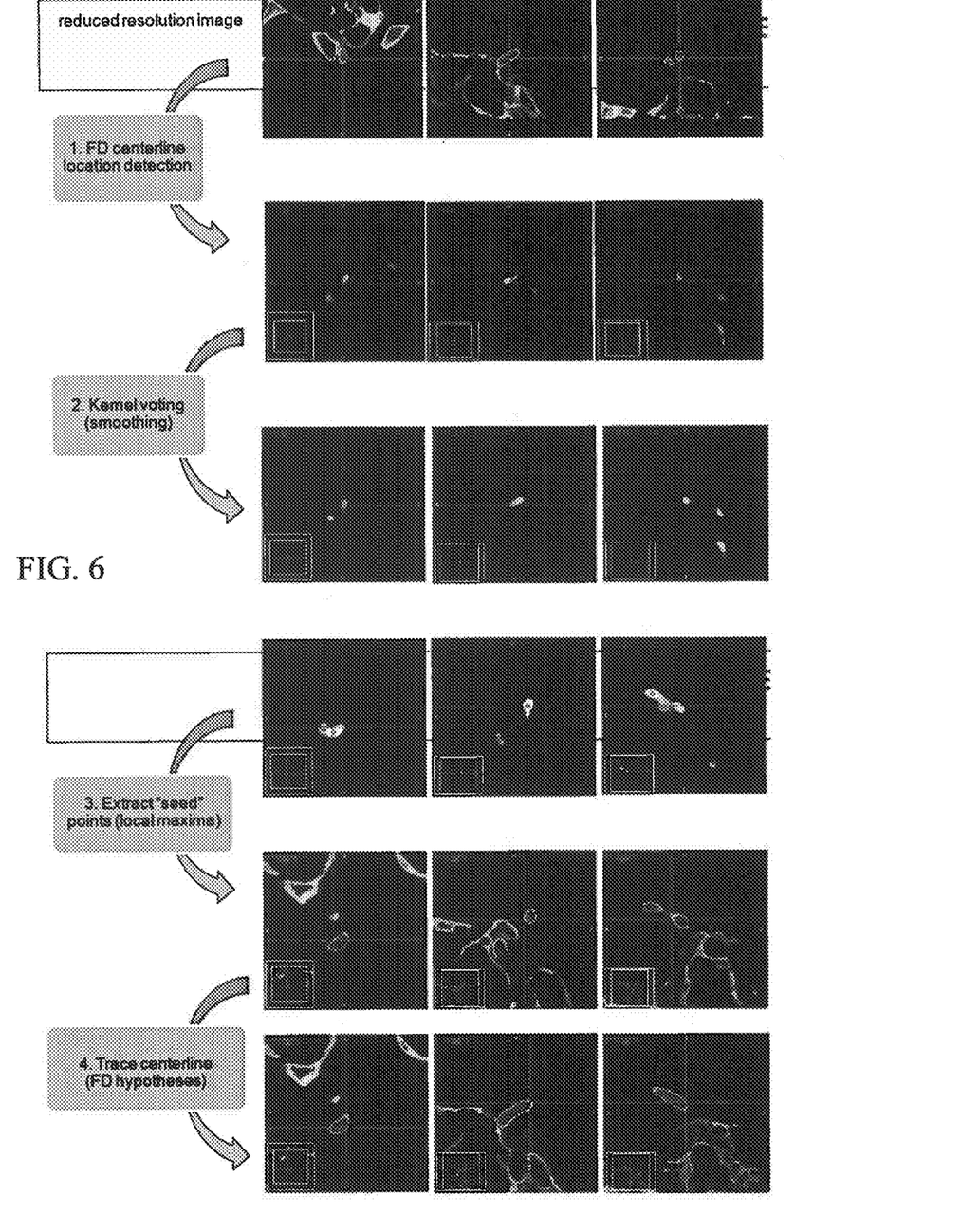
FIG. 6 illustrates a sequence of data processing for diverter detection using three example images.

To limit the number of locations tested, only the obtained data with higher intensities is tested. For example, FIG. 6 shows a top row of three images with reduced resolution and the high intensity data shown as bright relative to the background gray and black. Just the bright locations are tested. The second row shows respective response maps. Locations not likely to be a centerline are mapped to black, other value, or range of values. Locations possibly being centerlines are mapped to other shades corresponding to the likelihood.

The response map may be used as is or further processed for detection. For example, the response map is low pass filtered. Gaussian or other kernel-based smoothing may be used. Other filtering may be used. Isolated locations are less likely to be flow diverters, so the filtering removes those locations. The third row of FIG. 6 shows example response maps after filtering.

To further reduce the number of possible centerline locations, one or a few locations are selected from grouped locations. Since a centerline is a line or curve, an area or volume of contiguous locations is not likely to have each location be a centerline point. Instead, local maxima are selected. The filtered or unfiltered response map is searched for local maxima. Any size of search region or space may be used. Depending on the size, more than one location in a continuous region may be identified. Any local maxima search function may be used. Alternatively, the number of possible centerline locations is not reduced.

The fourth row of FIG. 6 shows identification of local maxima as dark dots within the bright regions. The fifth row of FIG. 6 shows the identified local maxima as dots placed relative to the obtained data (e.g., the preprocessed reduced resolution data). The local maxima are used as seed points for fitting the geometrical shape model. These seeds are identified as the hypotheses for possible locations of the flow diverter in act 44 of FIG. 4. Any number of locations for a given volume may be identified.

In act 26 of FIG. 3, a centerline score is calculated for each of the possible flow diverters. The score may be calculated for any of the locations whether identified as a possible flow diverter centerline point or not.

The score represents a measure of appearance. In one embodiment, the score is a likelihood or probability of the flow diverter being centered at the location. The centering may be with respect to a volume or with respect to a planar cross-section. The response map generated by a machine-trained detector indicates the probabilities at the different locations. The probability output of the machine-learned or other detector may be the score. The detector response at a location indicates the likelihood that a flow detector appears and is centered at the particular location. The response at the voxel corresponding to the location of the centerline point is used as the centerline score. Alternatively, other measures, such as an output of a separate classifier, are used to determine the scores for the locations.

The score, such as the probability of the centerline points, is used to detect the flow diverter. The score is determined for different locations. Different possible flow detectors have different centerline scores. Where the local maxima are identified, one centerline score may be provided for each possible flow diverter.

More than one score may be provided for a same possible flow diverter. For example, multiple local maxima for a same centerline may be identified and scored. As another example, as part of tracing to find a complete centerline for each possible flow diverter, scores may be determined for various sample points or centerline points once the tracing occurs. Centerline point scores are calculated for a plurality of centerline points along a given centerline.

In act 46, the flow diverter model is fit to the obtained data. The fitting includes identifying the centerline and corresponding surface points. Additional, different, or fewer geometrical components may be fit. Once identified, the orientation is verified in act 48.

In act 28, the direction of the centerline passing through the centerline points is determined. This determination occurs for each of the possible flow diverters, as represented by the loop from act 30 to act 28. The loop may include calculating a score for centerline points sampled along the traced centerline.

The local maxima or seed centerline points are used to trace and establish hypotheses of flow diverters with approximate estimation of centerline points and varying radius along the centerline. Once a centerline seed hypothesis is established, a model fitting step is performed to obtain a refined geometrical shape model of the flow diverter.

The centerline may be determined using region shrinking, skeletonization, or other process. In one embodiment, a machine-learnt detector is applied. A cross-section detector is learned from training images of flow diverters. The cross-section is orthogonal to the centerline. Given the ground truth images of flow diverters, cross section images are generated from the flow diverters as positive training samples. Negative samples are generated by perturbing the flow diverter parameter $(x,r,\theta)$.

The cross-section detector is a same or different type of machine-learnt detector as described above for the centerline detector. The same or different input features may be used. For example, two-dimensional Haar features, gradients, and consistent features are used. Two-dimensional Haar features and gradient features reflect that points on the cross section have a high chance of strong contrast to the surrounding. The consistent feature reflects the consistence property of points on the cross section. The points on the cross section are consistent along the flow diverter surface (i.e., outside of the cross-section plane). Points on other structures, such as bones, have different consistency compared to these flow diverter points on the cross section. Since a plane and surface points along a surface are being searched, the features are two dimensional instead of three dimensional.

The trained cross-section detector is applied to various possible cross-sections along different search directions from a seed or centerline point. Any sample step size in angle (e.g., direction) or distance (e.g., radius) may be used. Various possible cross-section planes are identified and tested. The cross-section detector computes the probability of surface points in the cross section plane $p(cs_i|cl_i,\Phi)$. The cross-section with the greatest probability, within any limitations on the amount of curvature of the centerline and/or circumference, indicates the direction of the centerline.

The next centerline sample is a given distance along the direction. For example, the direction with the greatest combined probabilities from the centerline detector and cross-section detector is determined as the direction to trace. This tracing is repeated until all of the probabilities associated with points not on the already determined centerline are below a threshold.

Figure 7A:
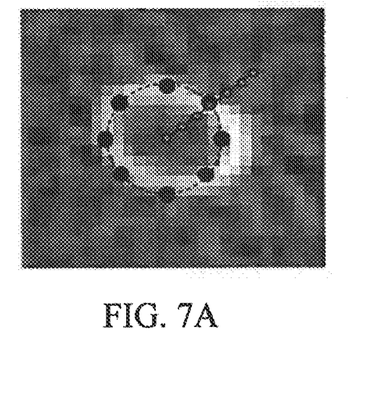
FIG. 7A shows an example cross-sectional image of a flow diverter.
Figure 7B:
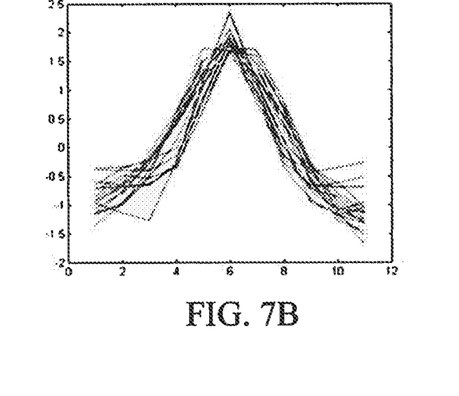
FIG. 7B shows example intensity profiles along different radii intersecting dots shown in FIG. 7A.

In another embodiment, a match filter is applied instead of a machine-trained cross-section detector. For a match filter, an expected intensity profile from a location in the flow diverter (e.g., centerline point) to a location outside the flow diverter is provided. The profile is along a one-dimensional line, such as along the surface normal. FIG. 7A shows eight surface sample points and one line for an intensity profile. The expected intensity profile may be experimentally or theoretically determined. For each tested cross-section, the intensity profile at a number (e.g., eight) of different angles is determined. The number is the number of surface points to test. For each surface point, an intensity profile is generated as shown in FIG. 7B.

The actual intensity profiles are compared to the expected intensity profile. A match filter is designed to respond to the pattern of intensity profile of the surface points. For example, a one-dimensional correlation is determined for each profile. An average, median, mode, or other statistic of the different matching represents the degree of matching for the possible cross-section.

By comparing cross-section information from possible directions about each possible centerline point, the centerline point along the centerline is determined. The cross-section with the best match, highest correlation, or greatest probability indicates the direction of the centerline and corresponding location of the next centerline point. The direction of the centerline from the seed or previous centerline point is determined by identifying the best cross-section. The process continues to determine the direction of the centerline for additional sample points.

Figure 8:
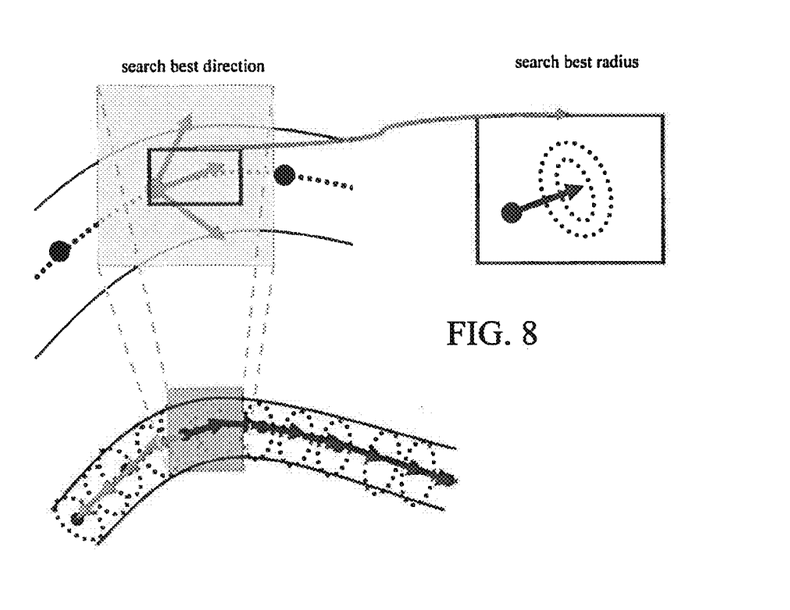
FIG. 8 illustrates one embodiment of a tracing process for detecting the flow diverter.

FIG. 8 shows this tracing using the cross-section detector. Starting from one centerline control point, the centerline is traced in the centerline detection map. The surface part, which is related to the cross section, is optimized. The best parameter of the cross section is identified. In the experiment, using grid directions and radii is one effective and efficient way to search the optimal parameter of the cross section locally. Other approaches may be used. For example, the centerline detector is used with skeletonization of the response map to find the centerline.

In one embodiment, the centerline tracing is represented as:

1. Candidates of centerline points are first collected by the learned discriminative centerline detector.

2. Set trace step and centerline point probability threshold $\tau$, search angle threshold $\theta_{r1}, \theta_{r2}$ $$\left( e.x. \; \theta_{t1} = -\frac{2\pi}{3}, \theta_{t2} = \frac{2\pi}{3} \right);$$

Set radius search grid r (limit as 0.5<r<2.5);

2. Visit the centerline point candidate pool (e.g., seeds)

2.1 Get one centerline point candidate located at x 2.2 Calculate search directions $\theta_1, \theta_2$, where $\theta_1, \theta_2$ are complementary, by:

A: Search the best parameter $(\hat{r}, \hat{\theta})$ (e.g., match filter or cross-section detector) to fit the cross section located at x, $$(\hat{r}, \hat{\theta}) = \operatorname*{argmax}_{(r,\theta)} P(cs_i \mid cl_i), \text{ then } \theta_1 = \hat{\theta}$$

2.3 Start from x and search around direction $\theta_1$ (finding centerline in one direction from seed point), begin loop 2.3.1 compute $p(cl_i=x)$, if $p(cl_i=x)<\tau$, stop the loop, otherwise continue, 2.3.2 A: search the optimal next centerline point $\hat{x}$ by $$(\hat{x}, \hat{r}, \hat{\theta}) = \operatorname*{argmax}_{(x,r,\theta)} P(cs_i \mid cl_i = x + \Delta_s \times \theta),$$

where $$\theta_{t1} < \text{angle}\,(\theta, \theta_1) < \theta_{t2}$$

2.3.3 set the next centerline point as: $x=x+\Delta_s \times \hat{\theta}$ 2.4 Start from x and search around direction $\theta_2$ (finding centerline in one direction from seed point), begin loop 2.4.1 compute $p(cl_i=x)$, if $p(cl_i=x)<\tau$, stop the loop, otherwise continue 2.4.2 A: search the optimal next centerline point $\hat{x}$ by $$(\hat{x}, \hat{r}, \hat{\theta}) = \operatorname*{argmax}_{(x,r,\theta)} P(cs_i \mid cl_i = x + \Delta_s \times \theta),$$

where $$\theta_{t1} < \text{angle}(\theta, \theta_2) < \theta_{t2}$$

2.4.3 set the next centerline point as: $x=x\Delta_s \times \hat{\theta}$ 2.5 Combine these two flow diverter component parts of the centerline to get one flow diverter centerline candidate;

The tracing repeats along the different directions for a given possible flow diverter. The tracing is repeated for each of the possible flow diverters. The direction determination along the centerline, centerline point score calculation, and cross-section score calculation repeat.

This process is performed for each possible flow diverter. Where centerlines from different possible flow diverters are close, such as within a radius or other distance indicating confusion or the same centerline, one may be eliminated. The centerline with the lesser centerline and/or surface probabilities is discarded.

The result of tracing is a centerline with greater likelihood or probability surface points. FIG. 6 shows the last row with the detected centerlines indicating each of the possible flow diverters.

In act 30, a cross-section score is calculated for each of the possible flow diverters. The cross-section score is a value representing whether the shape and/or appearance at a cross-section to the centerline matches the flow diverter geometric model. The direction of the centerline indicates the cross-sectional plane. The cross-section score is a ranking for that view of the cross-section of the possible flow diverter at that centerline point. The obtained data is used to determine the similarity with the model.

The score is a likelihood, probability, rating, priority, or other scoring. Any calculation may be used. The score is calculated separately from the tracing or is an output or calculation used in the tracing.

In one embodiment, the score is the sum of the correlations for the selected cross-section for a center point. The matching score or output of the matched filtering is used as the score.

The correlation indicates a probability or likelihood that the flow diverter cross-section is at that location.

In another embodiment, the output of a machine-learnt detector is used as the score. The machine-learnt detector indicates a probability of a match in the cross-section. Any machine-learnt detector may be used, such as the detector used to determine the direction and corresponding cross-section. In alternative embodiments, a different detector is used.

A cross-section score is determined for each of the possible flow diverters. For example, the cross-section score at the seeded centerline point is used. As another example, an average, sum, or other combination of cross-section scores from a plurality of centerline points is used. The cross-section score for a given possible flow diverter represents a combination of scores for the surface or circumference at different sample points along the possible flow diverter.

In act 32, one or more possible flow diverters are selected as representing the actual flow diverter. Where more than one flow diverter is implanted, more than one flow diverter may be detected. The method, informed by the user, selects the appropriate number of flow diverters. Alternatively, the flow diverters with the greatest or sufficient scores are selected for presentation to and further selection by the user. In other embodiments, a single possible flow diverter is selected.

The selection is a function of the centerline and cross-correlation scores. Any combination of scores may be used. For example, the centerline and corresponding cross-correlation scores are summed or multiplied. The results of such combination for different centerline points are summed. For example, the flow diverter probability is the sum of the products of the centerline and cross-correlations scores. The result is an overall score for the entire possible flow diverter. Other functions may be used.

In one embodiment, the flow diverter score is represented as $$P(FD) \propto \sum_{i=1}^{M} P(cs_i \mid cl_i) + P(cl_i).$$

The best flow diverter candidate is selected as the maximum from all the flow diverter candidates, represented as:

$$\hat{FD} = \mathrm{argmax} P(FD) \propto \mathrm{argmax} \sum_{i=1}^{M} P(cs_i \mid cl_i) + P(cl_i).$$

The possible flow diverter with a greatest flow diverter probability is selected. The selection is verification of the hypothesis as the flow diverter or as a false detection.

In one embodiment, the selection is part of a probabilistic framework. The flow diverter segmentation operates in a probabilistic framework. In this framework, the probability of flow diverter $FD=\{cl_i^\Phi, cs_i | i=1, \ldots, M\}$ is denoted by $P(FD)$. The location and shape of a flow diverter are estimated as the candidate that maximizes the probability:

$$\hat{FD} = \mathrm{argmax}_{\varphi} P(FD^\varphi).$$

As a curved tube, the flow diverter is a complex object in a high-dimensional space. Given M centerline points and corresponding surface points, the local image appearance of the centerline and surface points follow an identical likelihood model. Under this assumption, the probability of flow diverter $P(FD)$ is computed from measurement of individual centerline points and corresponding surface points as following:

$$P(FD^\Phi) = \Pi_{i=1}^{M} P(cl_i^\Phi, cs_i) = \Pi_{i=1}^{M} P(cs_i | cl_i^\Phi)$$
$$P(cl_i^\Phi) \propto \Sigma_{i=1}^{M} P(cs_i | cl_i^\Phi) + P(cl_i^\Phi)$$

where $P(cl_i^\Phi)$ is the probability of centerline point $(cl_i^\Phi)$, and $P(cs_i | cl_i^\Phi)$ is the probability of surface points on the cross section plane centered at point $cl_i^\Phi$. The flow diverter segmentation is simply to maximize the probability of flow diverter candidates as the form of:

$$\hat{FD} = \mathrm{argmax}_{\varphi} P(FD^\varphi) \propto \mathrm{argmax}_{\varphi} \sum_{i=1}^{M} P(cs_i \mid cl_i^\varphi) + P(cl_i^\varphi)$$

In act 34, an image of the flow diverter is generated from the obtained data, such as from the x-ray data obtained with a C-arm or in a computed tomography reconstruction. The image may be from other data. Other information may be included, such as graphic overlays or image data from other modalities of imaging.

The image is a function of the locations of the flow diverter. The locations indicate which data to alter. The locations are highlighted relative to the background. For example, the background intensities are reduced. As another example, the intensities for the flow diverter are increased. Other highlighting may include a graphic overlay and/or mapping to different color, shade, or brightness. Any alteration of the image to make the flow diverter more visible than when just using the reconstruction without alteration may be used.

In one embodiment, the image is generated with visualization changes. Using the intensities from the flow diverter locations (e.g., flow diverter surface), the dynamic range or sub-set associated with the flow diverter is determined, such as using a histogram. The average or other intensity associated with the flow diverter locations is used as the center for a limited range of intensities to be included in the image or to be altered differently. The dynamic range of the image is set based on the selected flow diverter information. Other dynamic range windowing may be used.

Combinations of windowing and changing intensity relative to the background may be used. In one embodiment, surrounding tissues are removed or reduced, and auto-windowing of the dynamic range is used. Once the flow diverter is localized and the 3D shape model is obtained, surrounding tissues are removed by setting the intensity to zero for all the voxels that are not in a close neighborhood (e.g., number of voxels or distance) of the flow diverter. In addition, the histogram of the intensity values of surface points is used to automatically compute a set of windowing parameters (e.g., size or interval of range and value location of the range) to achieve optimal visualization of the flow diverter.

Other visualization changes may be used alternatively or additionally. For example, a mesh or continuous function is fit to the shape model. This fit model may be imaged.

Any type of image may be generated. For example, the image is three-dimensionally rendered. Using a user or processor selected point of view with or without a lighting model, the data representing the flow diverter with or without surrounding tissue is rendered to a two-dimensional display. Any volume rendering may be used, such as projection or surface rendering. In another example, a planar reconstruction is generated from the data. A user or processor placed slice plane or image plane is positioned relative to the volume. The data representing or interpolated to represent the plane is used to generate the two-dimensional image. For multi-planar reconstruction, multiple planes are defined through the volume. An image is generated for each plane.

The image is shown alone. A sequence of such images may be shown, such as rendering from a sequence of volumes from implantation and from a follow-up. Alternatively, the image or images are shown with other information. The image may be separate but share the display screen with an image generated from the shape model. The model may be overlaid on the image, such as rendering the model with a different color, brightness or other characteristic. The rendered model is added to the image.

In alternative or additional embodiments, the flow diverter information is used for quantification. A volume, area, length, curvature, flow differential, or other quantity is calculated using the locations and/or shape of the flow diverter. For example, flow is measured at an entrance to the flow diverter and at an exit of the flow diverter using spatially registered ultrasound. The difference may represent leakage to the aneurysm. X-ray or other modality may be used to measure a fluid volume adjacent to but not within the flow diverter. The flow diverter locations are used as a reference to find and measure the aneurysm.

FIG. 9 shows a system for flow diverter detection. The system includes a medical imaging system 11, a processor 12, a memory 14, and a display 16. The processor 12 and the memory 14 are shown separate from the medical imaging system 11, such associated with being a computer or workstation apart from the medical imaging system 11. In other embodiments, the processor 12 and/or memory 14 are part of the medical imaging system 11. In alternative embodiments, the system is a workstation, computer, or server for detecting the flow diverter from data acquired by a separate system in real-time or using previously acquired patient-specific data stored in a memory. For example, the medical imaging system 11 is provided for acquiring data representing a volume, and a separate database, server, workstation, and/or computer is provided for detecting the flow diverter. Additional, different, or fewer components may be used.

The computing components of the system, such as the medical imaging system 11 and/or the processor 12 are configured by hardware, software, and/or design to perform calculations or other acts. The computing components operate independently or in conjunction with each other to perform any given act. The act is performed by one of the computer components, another of the computing components, or a combination of the computing components. Other components may be used by the computing components to scan or perform other functions.

The medical imaging system 11 is any now known or later developed modality. The medical imaging system 11 scans the brain for detection of the flow diverter within the patient. For example, a C-arm x-ray system (e.g., DynaCT from Siemens), CT like system, or CT system is used. Other modalities include MR, x-ray, angiography, fluoroscopy, PET, SPECT, or ultrasound. The medical imaging system 11 is configured to acquire the medical imaging data for flow diverter detection. The data is acquired by scanning the patient and/or by receiving signals from the patient.

The memory 14 is a buffer, cache, RAM, removable media, hard drive, magnetic, optical, database, or other now known or later developed memory. The memory 14 is a single device or group of two or more devices. The memory 14 is within the system 11, part of a computer with the processor 12, or is outside or remote from other components.

The memory 14 stores the reconstructed data, such as x-ray data of a volume representing a brain region. The data represents a three-dimensional region. Any format may be used, such as voxels interpolated to a three-dimensional grid or data representing parallel or non-parallel planes. The memory 14 stores data resulting from processes, such as storing the scores, locations, hypotheses, or other flow diverter detection information.

The memory 14 is additionally or alternatively a non-transitory computer readable storage medium with processing instructions. The memory 14 stores data representing instructions executable by the programmed processor 12 for flow diverter detection. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical data. The processor 12 is a single device, a plurality of devices, or a network. For more than one device, parallel or sequential division of processing may be used. Different devices making up the processor 12 may perform different functions, such as centerline detection by one detector and a separate device for performing cross-section scoring. In one embodiment, the processor 12 is a control processor or other processor of the medical imaging system 11. The processor 12 operates pursuant to stored instructions to perform various acts described herein.

The processor 12 is configured to detect the flow diverter from data of the scan by the medical imaging system 11. The detection is a function of likelihoods corresponding to different geometrical components of the flow diverter. For example, the centerline and cross-section or surface of the flow diverter are used to determine likelihoods. The appearance and shape are used probabilistically to detect the flow diverter. Possible flow diverters are detected using the centerline and the cross-section. Other geometrical characteristics of the flow diverter may be used. The processor 12 selects one of the possible flow diverters using the likelihoods from the different geometric components.

The processor 12 may perform machine learning and/or applies a machine-learnt algorithm. For example, the processor 12 applies a probabilistic model to detect centerline points and/or cross-sections. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

For application, the processor 12 calculates features for classification. The same or different features are used for classification of different geometric components. The features are three, two, and/or one-dimensional features. A window function defining the data is a cube, but may have other volume shapes. The window is translated, rotated, and/or scaled as part of searching for the flow detector.

Any features may be used. Different types of features may be used for the same classifier, or all of the features are of a same type for a given classifier. In one embodiment, Haar wavelet-like, gradient, consistency gradient, and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. "Steerable" features indicate a gradient along a specific direction. Other types of features may alternatively or additionally be used.

The processor 12 is configured to generate an image. The image is generated as a function of the detected flow diverter. The image is a volume or three-dimensional rendering. Alternatively, the image is of an arbitrarily positioned plane or planes through the volume. The plane or planes may have any orientation, including orientations within the volume different than the scanning lines or planes. In other embodiments, the image is of a model fit to the detected flow diverter.

The display 16 is a CRT, LCD, plasma, projector, printer, or other output device for showing an image. The display 16 displays an image of the flow diverter and/or a measure using the detected flow diverter. The measure may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for flow diverter detection in medical imaging, the method comprising:
   identifying, with a processor, locations of centerline points of possible flow diverters from x-ray data representing a volume including the flow diverter;
   calculating a centerline score for each of the possible flow diverters, the centerline score being a function of the location for the respective centerline point;
   determining, with the processor, directions of centerlines passing through the centerline points for each of the possible flow diverters;
   calculating a cross-section score for each of the possible flow diverters, the cross-section score being a function of the direction for the respective centerline;
   selecting a first one of the possible flow diverters as representing the flow diverter, the selecting being a function of the centerline scores and the cross-section scores; and
   generating an image of the flow diverter from the x-ray data, the flow diverter being the selected first of the possible flow diverters highlighted relative to a background.

2. The method of claim 1 further comprising obtaining the x-ray data as a normalized resolution secondary reconstruction limited to higher intensities.

3. The method of claim 1 wherein identifying comprises applying a machine-learned orientation invariant segment detector to Haar, gradient, or Haar and gradient features from the x-ray data.

4. The method of claim 3 wherein calculating the centerline score comprises determining an output of the machine-learned orientation invariant segment detector for the location.

5. The method of claim 1 wherein identifying comprises generating a response map with scores for voxels of the x-ray data, filtering the response map, and identifying each location of the locations of the centerline points as a local maximum in the filtered response map.

6. The method of claim 5 wherein calculating the centerline score comprises using the score for the voxel corresponding to the location.

7. The method of claim 1 wherein calculating the centerline score for each of the possible flow diverters comprises calculating a likelihood of the flow diverter being at the location.

8. The method of claim 1 wherein determining the direction comprises comparing cross-section information from possible directions about the centerline point and selecting the direction from the possible directions as a function of the comparing.

9. The method of claim 1 wherein determining the direction comprises applying a machine-learnt detector, and wherein calculating the cross-section score comprises determining an output of the machine-learnt detector.

10. The method of claim 1 wherein determining the direction comprises applying a match filter, and wherein calculating the cross-section score comprises calculating a correlation of the match filter.

11. The method of claim 1 wherein calculating the cross-section score comprises calculating the cross-section score from the x-ray data in a cross-section orthogonal to the direction at the centerline.

12. The method of claim 1 further comprising repeating the determining of the directions and calculating the cross-section score as a trace along the centerline for each of the possible flow diverters.

13. The method of claim 1 wherein calculating the centerline score for the possible flow diverter comprises calculating as a function of centerline point scores for a plurality of centerline points along the centerline for the possible flow diverter, and wherein calculating the cross-section score for the possible flow diverter comprises calculating as a function of cross-section point scores for the cross-sections to the respective centerline points.

14. The method of claim 1 wherein the centerline and cross-section scores are probabilities, and wherein selecting comprises selecting the possible flow diverter with a greatest flow diverter probability, the flow diverter probability being a product of the probabilities of the centerline and cross-section.

15. The method of claim 1 wherein generating the image comprises reducing intensity of surrounding tissue, increasing intensity of the flow diverter, dynamic range windowing, or combinations thereof.

16. In a non-transitory computer readable storage medium having stored therein data representing instructions executable by a programmed processor for flow diverter detection, the storage medium comprising instructions for:

obtaining data representing a brain region of a patient;

detecting a flow diverter represented in the data as a function of appearance and three-dimensional shape of the flow diverter, the detecting comprising calculating scores for centerline points and cross-section regions for each of the centerline points from the data as the appearance and finding the centerline points and cross-section regions as the three-dimensional shape, the detecting performed for multiple hypotheses;

selecting one of the multiple hypotheses as a function of the scores; and outputting an image of the flow diverter, the image of the flow diverter being a function of locations of the detected flow diverter.

17. The non-transitory computer readable storage medium of claim 16 wherein obtaining comprises obtaining x-ray data, and wherein outputting comprises generating the image with background reduction, increasing of the locations, dynamic range windowing based on intensities at the locations, or combinations thereof.

18. A system for flow diverter detection, the system comprising:

a C-arm x-ray scanner configured to scan a patient with a flow diverter within the patient; and a processor configured to detect the flow diverter from data of the scan, the detection being a function of first and second likelihoods corresponding to first and second geometrical components of the flow diverter, the first geometrical component different than the second geometrical component;

wherein the processor is configured to detect the flow diverter by identifying possible flow diverters using centerline and cross-section as the first and second geometrical components and by selecting one of the possible flow diverters as a function of the first and second likelihoods for the possible flow diverters.

* * * * *